(12) United States Patent
Lober

(10) Patent No.: US 10,905,515 B2
(45) Date of Patent: *Feb. 2, 2021

(54) AUTOCLAVE-TOLERANT SURGICAL INSTRUMENT CONTAINERS AND CONTAINER SYSTEMS

(71) Applicant: OP-MARKS MEDICAL, LLC, East Hanover, NJ (US)

(72) Inventor: Stephen Bruce Lober, Athens, GA (US)

(73) Assignee: OP-MARKS MEDICAL, LLC, East Hanover, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/174,195

(22) Filed: Oct. 29, 2018

(65) Prior Publication Data

US 2019/0060021 A1 Feb. 28, 2019

Related U.S. Application Data

(63) Continuation of application No. 14/772,987, filed as application No. PCT/US2014/020348 on Mar. 4, 2014, now Pat. No. 10,111,710.

(Continued)

(51) Int. Cl.
*A61B 50/20* (2016.01)
*A61L 2/26* (2006.01)
(Continued)

(52) U.S. Cl.
CPC .............. *A61B 50/20* (2016.02); *A61B 50/33* (2016.02); *A61L 2/07* (2013.01); *A61L 2/26* (2013.01);
(Continued)

(58) Field of Classification Search
CPC .............................. A61B 50/20; A61B 50/33
(Continued)

(56) References Cited

U.S. PATENT DOCUMENTS 3,727,749 A 4/1973 Martin
4,753,345 A 6/1988 Goodsir et al.
(Continued)

FOREIGN PATENT DOCUMENTS

GB 2 407 505 A 5/2005

OTHER PUBLICATIONS

Outpatient Surgery Magazine. Product Showcase. Herrin Publishing Partners LP. May 2010. Retrieved from internet: <URL: http://www.outpatientsurgery.net/_media/pcp/print-article?id=8534>p. 5, lines 25-34.

(Continued)

*Primary Examiner* — Holly Kipouros
(74) *Attorney, Agent, or Firm* — Moser Taboada

(57) ABSTRACT

Containers and container systems for temporarily storing and/or securing one or more surgical instruments in a neutral position during a surgical procedure. The containers are configured to withstand autoclave sterilization such that the containers are reusable following autoclave sterilization. The container includes a syringe holder having an elongate body, at least one pair of spaced guard elements extending upwardly, at least one supporting element, and at least one row of spaced projections.

9 Claims, 21 Drawing Sheets

Related U.S. Application Data

(60) Provisional application No. 61/772,019, filed on Mar. 4, 2013.

(51) Int. Cl.
*A61B 50/33* (2016.01)
*A61L 2/07* (2006.01)
*A61M 5/00* (2006.01)

(52) U.S. Cl.
CPC ..... *A61L 2202/182* (2013.01); *A61L 2202/24* (2013.01); *A61M 5/002* (2013.01)

(58) Field of Classification Search
USPC .......................................................... 422/26
See application file for complete search history.

(56) References Cited

U.S. PATENT DOCUMENTS

| | | | |
|---|---|---|---|
| 5,195,538 A | 3/1993 | Eldridge, Jr. et al. | |
| 5,339,955 A | 8/1994 | Horan et al. | |
| 5,505,916 A * | 4/1996 | Berry, Jr. | A61L 2/06 422/300 |
| 5,540,901 A | 7/1996 | Riley | |
| 6,065,596 A | 5/2000 | Cavanagh | |
| 6,264,902 B1 | 7/2001 | Howlett | |
| 6,331,280 B1 * | 12/2001 | Wood | A61L 2/26 206/268 |
| 2001/0035362 A1 | 11/2001 | Odierno et al. | |

OTHER PUBLICATIONS

OP-Marks. OP-marks—OP=mark's Photos | Facebook. Facebook. Nov. 13, 2012. Retrieved from internet:<URL: https://www.facebook.com/132594923422158/photos/pb.132594923422158.-2207520000.1402065476./550744258273887/?type=1>.

International Search Report and Written Opinion dated Jun. 26, 2014 for PCT Application No. PCT/US2014/020348.

* cited by examiner

AUTOCLAVE-TOLERANT SURGICAL INSTRUMENT CONTAINERS AND CONTAINER SYSTEMS

CROSS-REFERENCE TO RELATED PATENT APPLICATIONS

This application is a continuation of U.S. application Ser. No. 14/772,987 filed Sep. 4, 2015 (now allowed as U.S. Pat. No. 10,111,710), which is a 35 U.S.C. 371 national application of PCT/US2014/020348 filed Mar. 4, 2014, which claims priority or the benefit of U.S. provisional Application No. 61/772,019, the contents of which are fully incorporated herein by reference in their entirety.

FIELD

This application relates to containers for holding surgical instruments, and, more particularly, to surgical instrument containers that are configured to withstand autoclave sterilization.

BACKGROUND

In order to prevent injuries during surgical procedures, current operating room practice requires that all "sharp" instruments, including, for example, scalpels, needles, skin hooks, and other sharp-ended instruments, to be securely placed within a "neutral zone" from which the instrument can be retrieved by another member of the operating room staff. No "sharp" instruments are transferred directly from one operating staff member (i.e., surgeon, first assistant, scrub technician, etc.) to another. Conventional surgical instrument containers are discarded as biohazard waste following the completion of a surgical procedure.

Accordingly, there is a need in the pertinent art for containers and container systems that provide a clearly delineated "neutral zone" for placement of surgical instruments. There is a further need in the pertinent art for containers and container systems that are re-useable and that can withstand autoclave sterilization.

SUMMARY

Described herein surgical instrument containers for securing at least one surgical instrument in a neutral position during a surgical procedure. The surgical instrument containers can be configured to withstand autoclave sterilization such that they are reusable following autoclave sterilization.

In one aspect, a surgical instrument container can comprise a syringe holder for securing at least one syringe in a neutral position during a surgical procedure. Each syringe can have a needle, a barrel, and a plunger.

The syringe holder can include an elongate body having a longitudinal axis, a top surface, and a bottom surface. The syringe holder can also include at least one pair of spaced guard elements extending upwardly relative to the top surface of the elongate body. Each guard element of each pair of guard elements can have first and second end portions and a longitudinal axis extending substantially parallel to the longitudinal axis of the elongate body. Each pair of spaced guard elements can cooperate to define a channel configured to receive at least a portion of the needle of a syringe.

The syringe holder can also include at least one supporting element extending upwardly relative to the top surface of the elongate body. Each supporting element can have a longitudinal axis extending substantially perpendicularly relative to the longitudinal axis of the elongate body. Each supporting element can be spaced from the first end portions of a pair of guard elements relative to the longitudinal axis of the elongate body such that the pair of guard elements and the supporting element cooperate to define a receiving space configured to receive at least a portion of the needle of a syringe.

The syringe holder can further include at least one row of spaced projections extending upwardly relative to the top surface of the elongate body. The spaced projections of each row can cooperate to define at least one channel configured to receive a portion of the barrel of the syringe. The plurality of projections can extend substantially perpendicularly relative to the longitudinal axis of the elongate body. Each channel defined by each row of spaced projections can be substantially axially aligned with the channel defined by a pair of spaced guard elements.

In another aspect, a surgical instrument container can comprise a surgical tray for temporary storage of one or more surgical instruments in a neutral position during a surgical procedure. The surgical tray has a longitudinal axis and can include a base portion having a top surface and a bottom surface. The base portion can define an outer periphery of the surgical tray.

The surgical tray can also include an outer wall extending upwardly relative to the top surface of the base portion. The outer wall can have opposed proximal and distal end portions and first and second opposed side portions. At least the side portions of the outer wall can be spaced relative to the outer periphery of the surgical tray.

The surgical tray can further include an inner portion positioned within the outer wall. The inner portion can have a top surface, a plurality of projections, and a plurality of through-holes. The outer wall can cooperate with the inner portion to define a cavity configured to receive the one or more surgical instruments. The plurality of projections and the plurality of through-holes can be spaced relative to the longitudinal axis of the surgical tray. Each through-hole of the plurality of through-holes can extend from the top surface of the inner portion to the bottom surface of the base portion.

BRIEF DESCRIPTION OF THE DRAWINGS

These and other features of the preferred embodiments of the invention will become more apparent in the detailed description in which reference is made to the appended drawings wherein.

DETAILED DESCRIPTION

Figure 1:
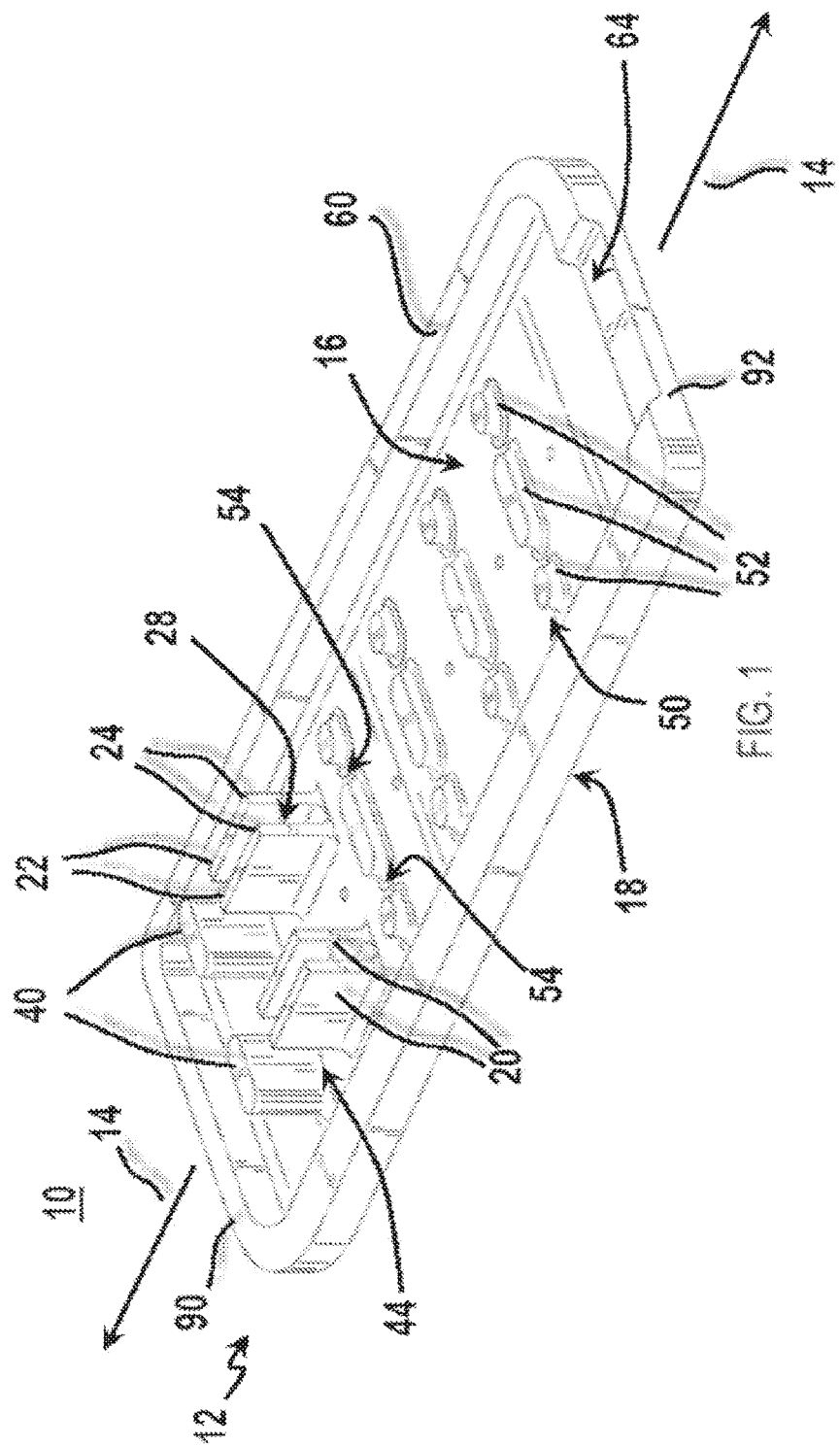
FIG. 1 is a perspective view of an exemplary syringe holder for receiving one or more syringes, as described herein.
Figure 2:
FIG. 2 is a front end view of the syringe holder of FIG. 1.
Figure 3:
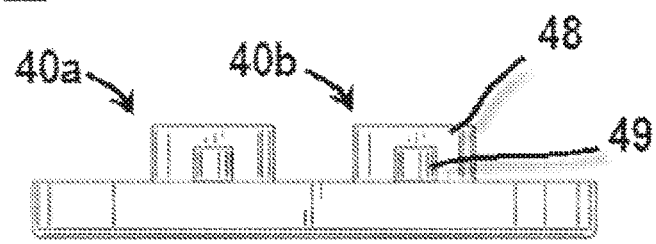
FIG. 3 is a back end view of the syringe holder of FIG. 1.
Figure 4:
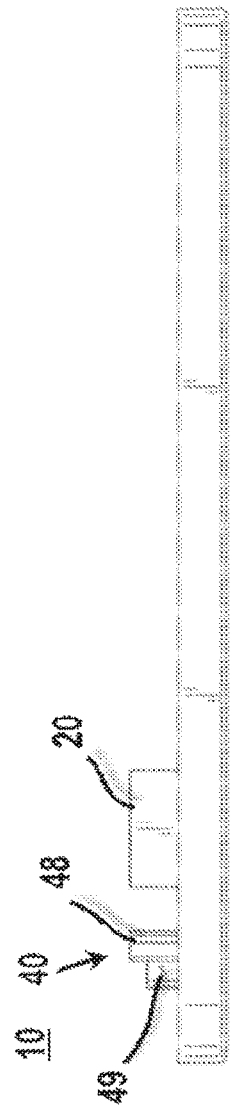
FIG. 4 is a left side view of the syringe holder of FIG. 1.
Figure 5:
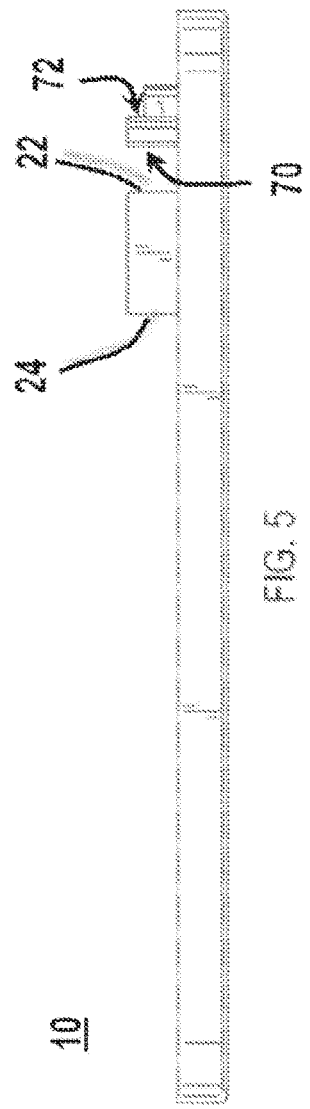
FIG. 5 is a right side view of the syringe holder of FIG. 1.
Figure 6:
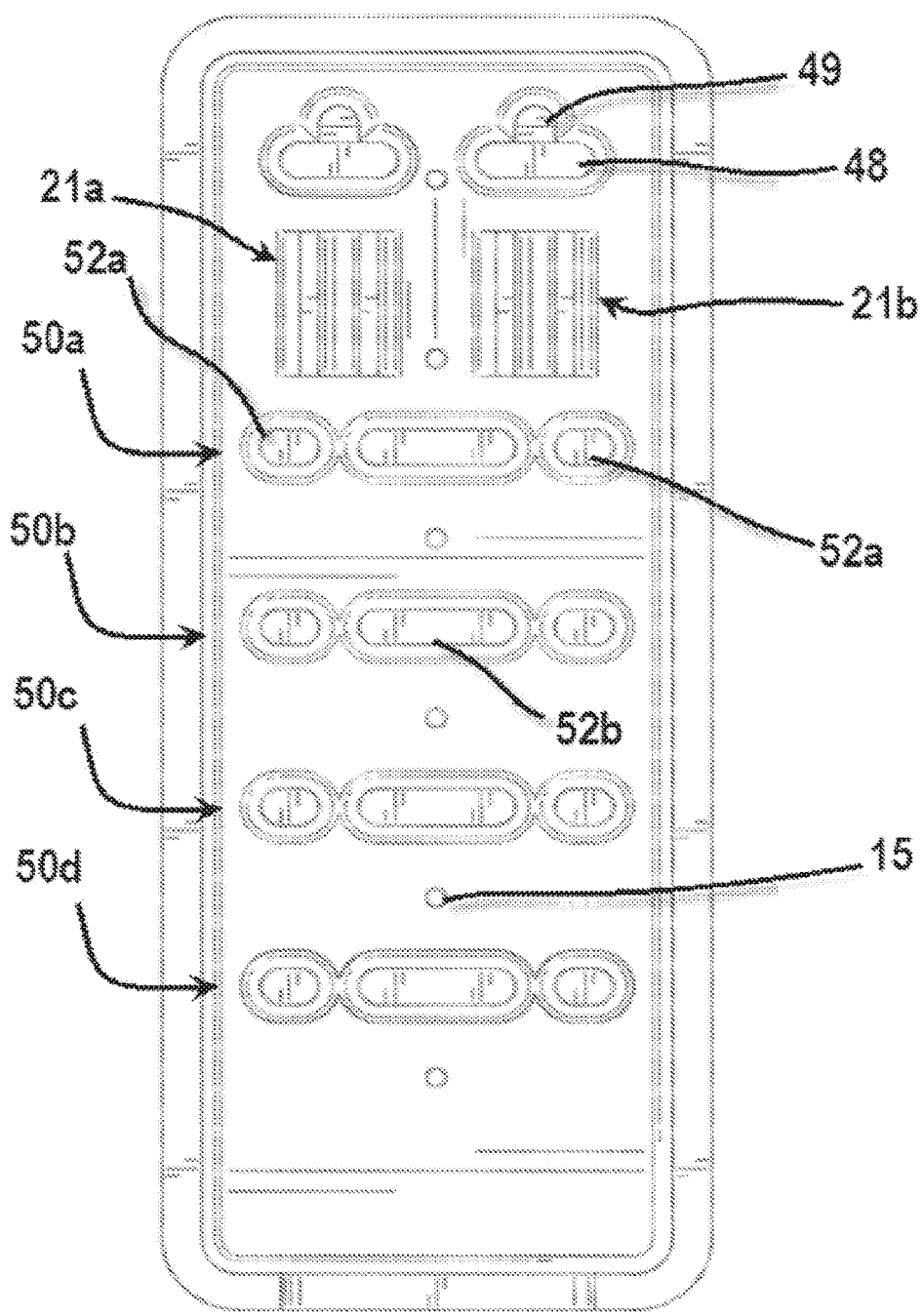
FIG. 6 is a top view of the syringe holder of FIG. 1.
Figure 7:
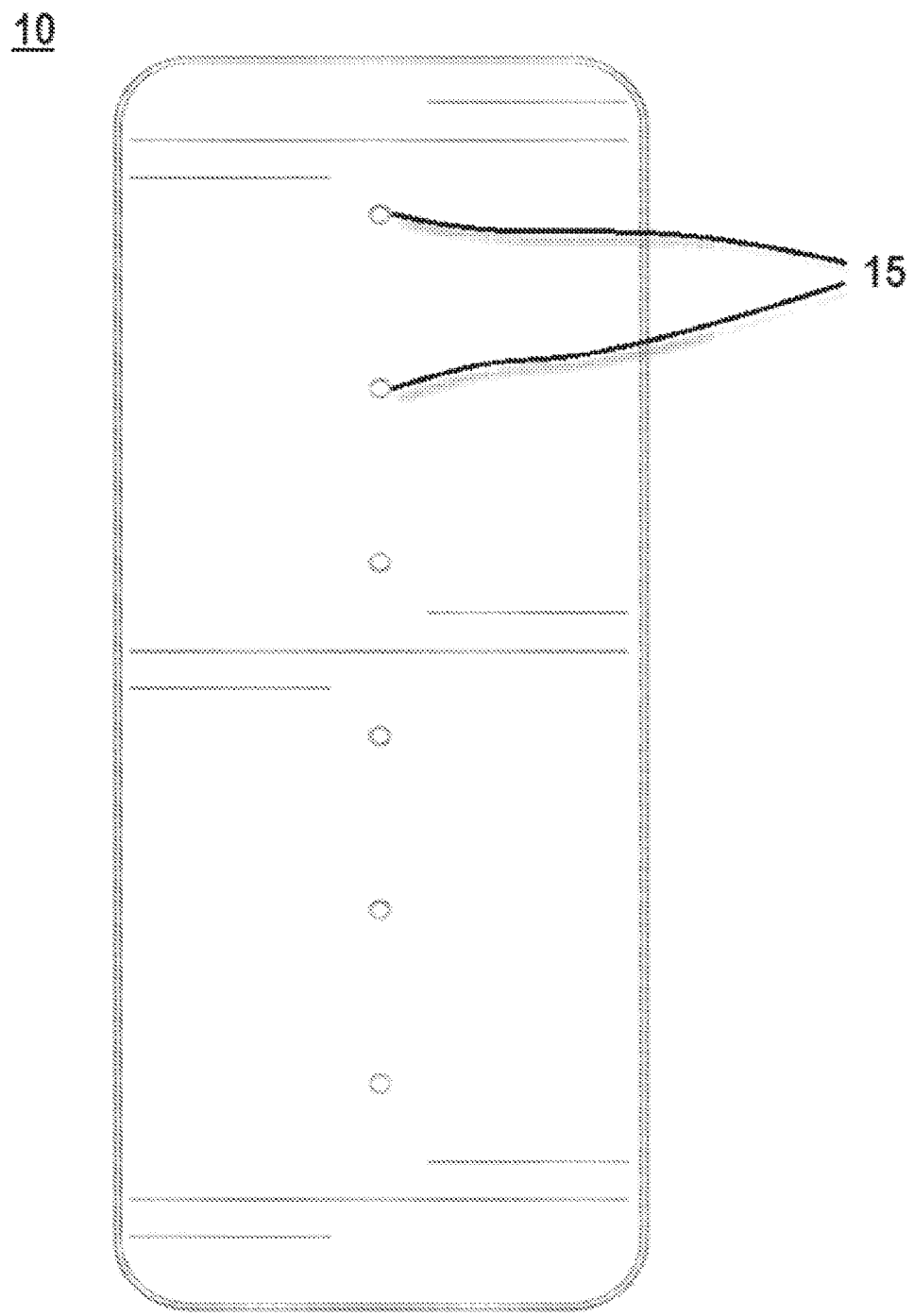
FIG. 7 is a bottom view of the syringe holder of FIG. 1.
Figure 8:
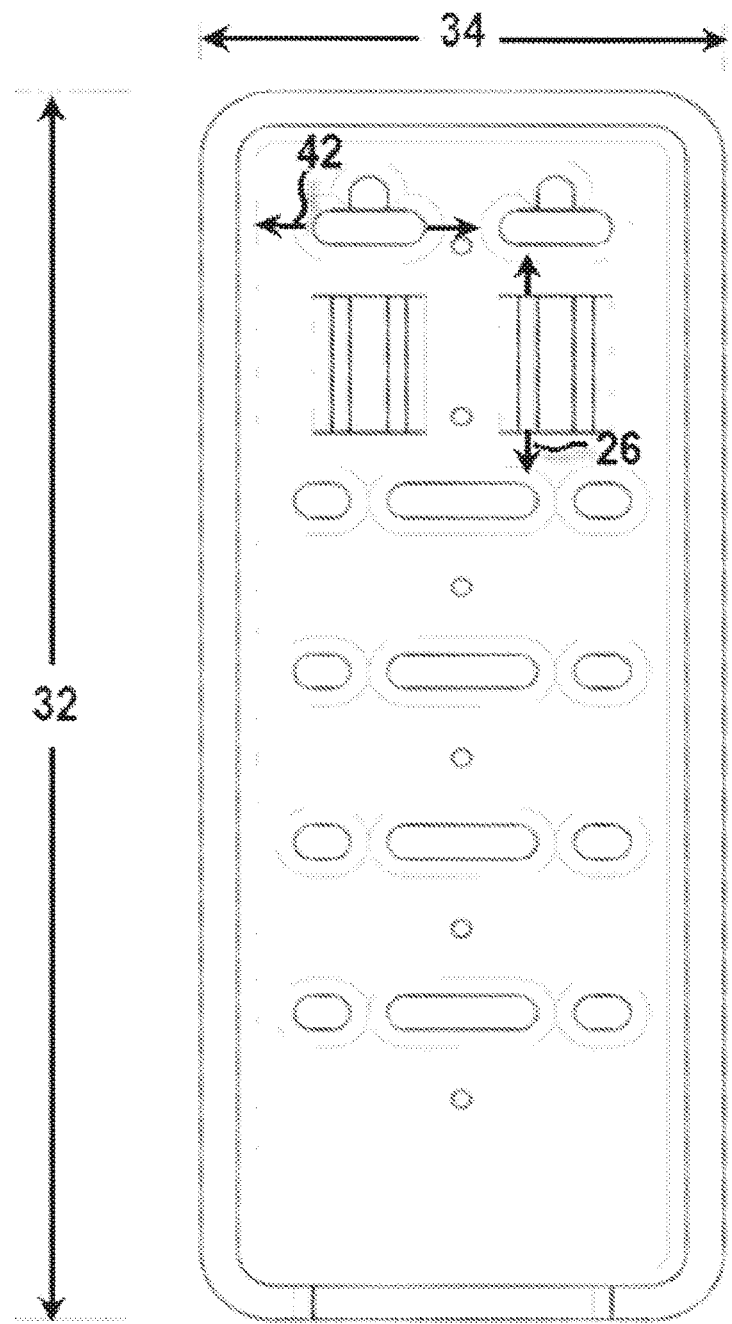
FIGS. 8-9 are top views of an exemplary syringe holder as described herein, showing exemplary dimensions of the syringe holder.
Figure 9:
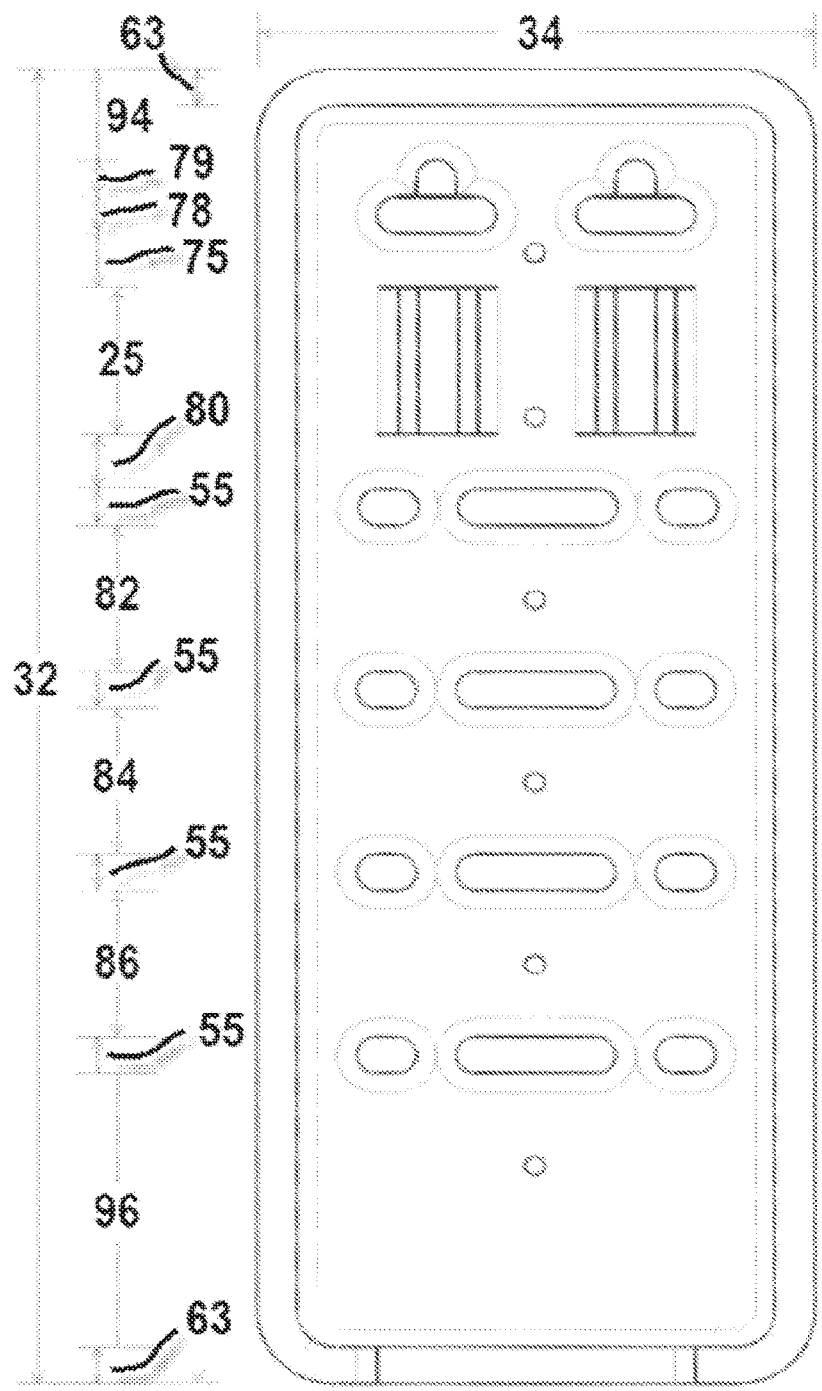
Figure 10A:
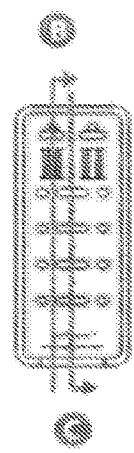
FIG. 10A is a top view of an exemplary syringe holder as described herein.
Figure 10B:
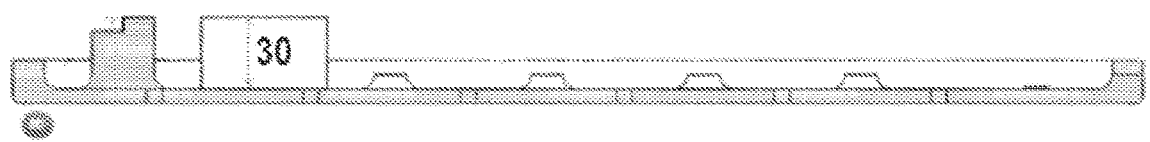
FIG. 10B is a longitudinal cross-sectional view of the syringe holder of FIG. 10A, taken along line B.
Figure 10C:
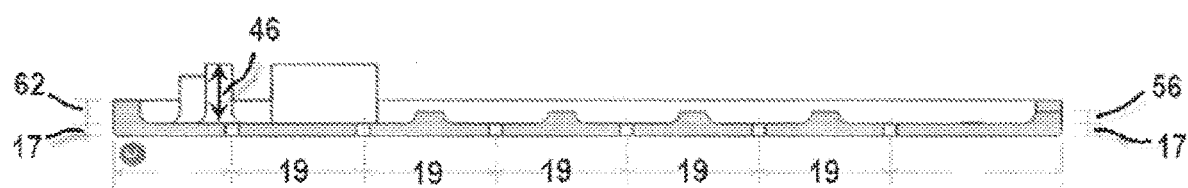
FIG. 10C is a longitudinal cross-sectional view of the syringe holder of FIG. 10A, taken along line C.
Figure 11:
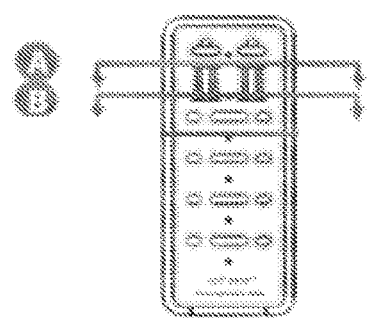
FIG. 11 is a top view of an exemplary syringe holder as described herein.
Figure 11A:
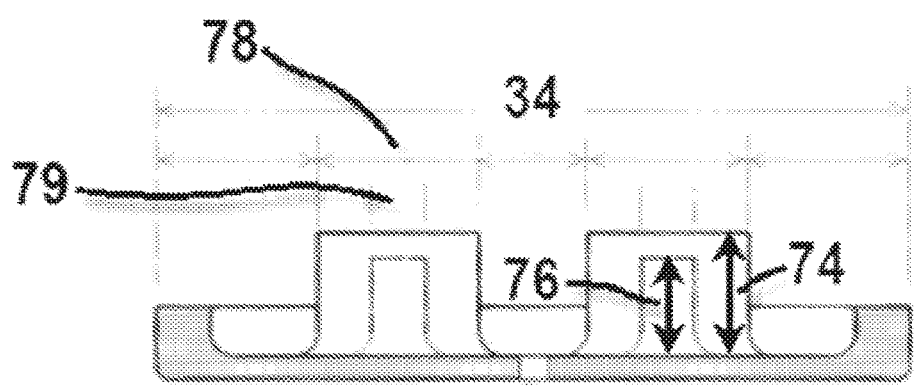
FIG. 11A is a transverse cross-sectional view of the syringe holder of FIG. 11, taken along line A.
Figure 11B:
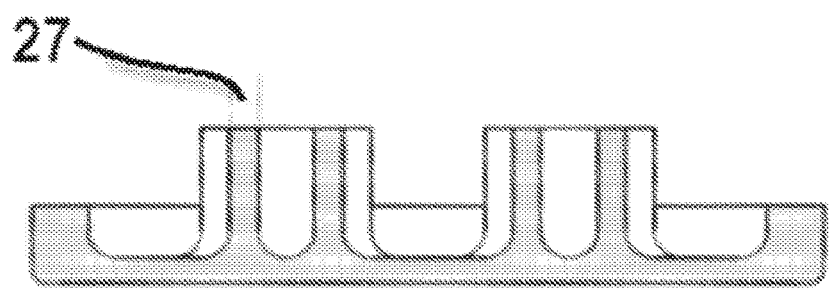
FIG. 11B is a transverse cross-sectional view of the syringe holder of FIG. 11, taken along line B.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a through-hole" can include two or more such through-holes unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

Described herein reference to FIGS. 1-21 are containers and container systems temporarily storing and/or securing one or more surgical instruments in a neutral position. As used herein, the term "neutral position" refers to a resting position of the surgical instrument before or after use of the surgical instrument during a surgical procedure.

The described containers can be autoclave-tolerant. As used herein, the term "autoclave-tolerant" refers to containers that are configured to withstand autoclave sterilization. As used herein, the term "autoclave sterilization" refers to any conventional autoclave sterilization process, including, for example and without limitation, steam autoclave processes, dry-heat autoclave processes, chemical vapor autoclave processes, and ethylene oxide autoclave processes. In exemplary aspects, the "autoclave sterilization" process can use high-pressure saturated steam and occur at a temperature of at least 121° C. and over a time period about 15 to about 20 minutes. However, it is contemplated that the autoclave process can occur at any temperature ranging from about 121° C. to about 190° C., at any pressure ranging from about 15 psi (pounds per square inch) to about 40 psi, and over any time period ranging from about 3 minutes to about 12 hours. It is contemplated that the autoclave-tolerant containers described herein can be reused after each autoclave sterilization procedure to reduce biohazard waste and decrease the operating costs of hospitals and other surgical facilities. It is further contemplated that the autoclave-tolerant containers can optionally comprise silicone, such as, for example and without limitation, TSE221 series silicone rubber (GE Toshiba Silicones Co., Ltd.).

Exemplary containers include syringe holders and surgical trays, as further described below. However, it is contemplated that the containers can have any shape or configuration that permits receipt of one or more surgical instruments and continued use of the containers following autoclave sterilization.

The Syringe Holder

In exemplary aspects, and with reference to FIGS. 1-11, a syringe holder 10 can be provided for securing at least one syringe in a neutral position. In these aspects, each syringe of the at least one syringe can be a conventional syringe having a needle, a barrel, and a plunger. However, it is contemplated that the syringe holder 10 can be configured to receive any known syringe.

In one aspect, the syringe holder 10 can have an elongate body 12 having a longitudinal axis 14, a top surface 16, and a bottom surface 18. In another aspect, the syringe holder 10 can have at least one pair 21 of spaced guard elements 20 extending upwardly relative to the top surface 16 of the elongate body 12. In this aspect, each guard element 20 of each pair 21 of guard elements can have first and second end portions 22, 24 and a longitudinal axis 26 extending substantially parallel to the longitudinal axis 14 of the elongate body 12. It is contemplated that each pair 21 of spaced guard elements 20 can cooperate to define a channel 28 that is configured to receive at least a portion of the needle of a syringe. Optionally, the channel 28 can be configured to receive the portion of the needle of the syringe in a jam or interference fit. It is still further contemplated that each spaced guard element 20 can have a respective height 30 relative to the top surface 16 of the elongate body 12. In exemplary aspects, the heights 30 of the spaced guard elements 20 of each pair 21 of spaced guard elements can be substantially equal. In these aspects, it is contemplated that the height 30 of each guard element 20 can range from about 0.1 inches to about 1 inch and, more preferably, can range from about 0.5 inches to about 0.75 inches. In exemplary aspects, the elongate body 12 can have a longitudinal length 32 (relative to the longitudinal axis 14) ranging from about 5 inches to about 15 inches and more preferably, ranging from about 8 inches to about 10 inches. In these aspects, the elongate body 12 can have a width 34 ranging from about 2 inches to about 6 inches and, more preferably, ranging from about 3 inches to about 5 inches. In further exemplary aspects, it is contemplated that each guard element 20 can have a longitudinal length 25 (relative to longitudinal axis 26) ranging from about 0.5 inches to about 1.5 inches and, more preferably, being about 1 inch. In still further exemplary aspects, it is contemplated that each guard element 20 can have a width 27 ranging from about 0.1 inches to about 0.2 inches.

In an additional aspect, the syringe holder 10 can comprise at least one supporting element 40 extending upwardly relative to the top surface 16 of the elongate body 12. In this aspect, each supporting element 40 of the at least one supporting element can have a longitudinal axis 42 extending substantially perpendicularly relative to the longitudinal axis 14 of the elongate body 12. It is contemplated that each supporting element 40 can be spaced from the first end portions 22 of a pair 21 of guard elements 20 relative to the longitudinal axis 14 of the elongate body 12 such that the pair of guard elements and the supporting element cooperate to define a receiving space 44 configured to receive at least a portion of the needle of a syringe. It is further contemplated that each supporting element 40 can be configured for engagement with a tip of the needle of a syringe to reduce the incidence of inadvertent needle pricks. It is still further contemplated that each supporting element 40 can have a respective height 46 relative to the top surface 16 of the elongate body 12. In exemplary aspects, the height 46 of each supporting element 40 can be substantially equal to the heights 30 of each spaced guard element 20.

In a further aspect, the syringe holder 10 can comprise at least one row 50 of spaced projections 52 extending upwardly relative to the top surface 16 of the elongate body 12. In this aspect, the spaced projections 52 of each row 50 can cooperate to define at least one channel 54 that is configured to receive a portion of the barrel of the syringe. It is contemplated that the plurality of projections 52 can extend substantially perpendicularly relative to the longitudinal axis 14 of the elongate body 12. It is further contemplated that each channel 54 defined by each row 50 of spaced projections 52 can be substantially axially aligned with the channel 28 defined by a pair 21 of spaced guard elements 20. It is still further contemplated that each projection 52 of the at least one row 50 of spaced projections 52 can have a respective height 56. In exemplary aspects, the height 56 of the projections 52 of the at least one row 50 of spaced projections can be substantially equal. In these aspects, it is contemplated that the height 56 of the projections 52 can range from about 0.05 inches to about 0.5 inches and, more preferably, from about 0.1 inches to about 0.2 inches. In additional aspects, it is contemplated that each projection 52 can have a longitudinal length 55 (measured relative to longitudinal axis 14) ranging from about 0.1 inches to about 0.5 inches and, more preferably, ranging from about 0.2 inches to about 0.3 inches.

In exemplary aspects, the elongate body 12 can comprise an outer wall 60 that extends upwardly relative to the top surface 16 of the elongate body. In these aspects, the outer wall 60 can have a height 62 relative to the top surface 16 of the elongate body 12. It is contemplated that the height 62 of the outer wall 60 can be less than the height 30 of the spaced guard elements 20 and the height 46 of the supporting elements 40. It is further contemplated that the height 56 of the projections 52 can be less than the height 62 of the outer wall 60. In exemplary aspects, the height 62 of the outer wall 60 can range from about 0.1 inches to about 0.75 inches and, more preferably, can range from about 0.2 to about 0.5 inches. In exemplary aspects, the outer wall 60 can have a thickness 63 ranging from about 0.1 inches to about 0.5 inches and, more preferably, ranging from about 0.2 inches to about 0.3 inches.

In one aspect, each supporting element 40 of the at least one supporting element 40 can comprise an engagement portion 48 and a stabilizing portion 49. In this aspect, the engagement portion 48 can extend substantially parallel to the longitudinal axis 46 of the supporting element 40. It is contemplated that the engagement portion 48 can define an engagement surface 70 and an opposed back surface 72. It is further contemplated that the engagement surface 70 can be spaced a predetermined distance 75 from the first end portions 22 of the guard elements 20 relative to the longitudinal axis 14 of the elongate body 12. In exemplary aspects, the predetermined distance 75 can range from about 0.1 inches to about 0.75 inches and, more preferably, can range from about 0.2 to about 0.5 inches. In another aspect, the stabilizing portion 49 can extend from the back surface 72 of the engagement portion 48 substantially perpendicularly relative to the longitudinal axis 46 of the supporting element 40. In this aspect, it is contemplated that the stabilizing portion 49 can have height 74 that is less than a height 73 of the engagement portion 48. In other aspects, it is contemplated that the engagement portion 48 and the stabilizing portion 49 of each supporting element 40 can have respective lengths 76, 77 (measured perpendicular to longitudinal axis 46) ranging from about 0.1 inches to about 0.5 inches and, more preferably, ranging from about 0.2 inches to about 0.3 inches. In exemplary aspects, it is contemplated that the engagement portion 48 of each supporting element 40 can have a width 78 (measured parallel to the longitudinal axis 46) ranging from about 0.5 inches to about 1 inch and, more preferably, from about 0.7 inches to about 0.8 inches. In these aspects, it is contemplated that the stabilizing portion 49 of each supporting element 40 can have a width 79 (measured parallel to the longitudinal axis 46) ranging from about 0.1 inches to about 0.2 inches.

In exemplary aspects, the at least one pair of spaced guard elements 20 can comprise two pairs 21a, 21b of spaced guard elements and the at least one supporting element 40 can comprise two supporting elements 40a, 40b. In these aspects, the two pairs 21a, 21b of the spaced guard elements 20 and the two supporting elements 41a, 41b can be evenly positioned on opposing sides of the longitudinal axis f the elongate body 12.

In additional exemplary aspects, each row 50 of the at least one row of spaced projections 52 can optionally comprise three projections. In these aspects, the spaced projections 52 can comprise two outer projections 52a and a central projection 52b. It is contemplated that the two outer projections 52a can be evenly positioned on opposing sides of the longitudinal axis 14 of the elongate body 12. It is further contemplated that the central projection 52b can optionally be substantially bisected by the longitudinal axis of the elongate body. In exemplary aspects, the central projection 52b can have a width (measured perpendicularly relative to the longitudinal axis 14 of the elongate body 12) that is greater than respective widths of the two outer projections 52a. In these aspects, it is further contemplated that the outer projections 52a of each row 50 can have substantially equal widths.

In further exemplary aspects, the at least one row 50 of spaced projections 52 can comprise four rows of spaced projections. In these aspects, a first row 50a of spaced projections can be spaced a predetermined distance 80 from the second end portions 24 of the pairs of spaced guard elements 20. It is contemplated that this predetermined distance 80 can range from about 0.1 inches to about 0.75 inches and, more preferably, can range from about 0.2 to about 0.5 inches. It is further contemplated that a second row 50b of spaced projections can be spaced a predetermined distance 82 from the first row 50a of spaced projections relative to the longitudinal axis 14 of the elongate body 12. It is further contemplated that a third row 50c of spaced projections can be spaced a predetermined distance 84 from the second row 50b of spaced projections relative to the longitudinal axis 14 of the elongate body 12. It is further contemplated that a fourth row 50d of spaced projections can be spaced a predetermined distance 86 from the third row 50c of spaced projections relative to the longitudinal axis 14 of the elongate body 12. It is still further contemplated that the predetermined distance 82 by which the second row 50b of spaced projections is spaced from the first row 50a of spaced projections can be substantially equal to the predetermined distance 84 by which the third row 50c of spaced projections is spaced from the second row 50b of spaced projections and the predetermined distance 86 by which the fourth row 50d of spaced projections is spaced from the third row 50c of spaced projections. In exemplary aspects, these predetermined distances 82, 84, 86 can range from about 0.5 inches to about 1.5 inches and, more preferably, can range from about 0.75 inches to about 1.25 inches.

In still further exemplary aspects, the elongate body 12 can have a first end portion 90 and a second end portion 92. In these aspects, the first end portion 90 can be spaced from the at least one supporting element 40 by a predetermined distance 94 relative to the longitudinal axis 14 of the elongate body 12, and the second end portion 92 can be spaced from the fourth (or otherwise most proximate) row of spaced projections by a predetermined distance 96 relative to the longitudinal axis 14. It is contemplated that the predetermined distance 94 between the first end portion 90 and the at least one supporting element 40 can range from about 0.1 inches to about 0.75 inches and, more preferably, can range from about 0.2 to about 0.5 inches. It is further contemplated that the predetermined distance 96 between the second end portion 92 and the most proximate row 50 of spaced projections 52 can range from about 1 inch to about 2.5 inches and, more preferably, can range from about 1.5 inches to about 2.25 inches. It is still further contemplated that the space between the most proximate (e.g., fourth) row of the spaced projections and the second end portion 92 of the elongate body 12 can be configured to receive at least a portion of the plunger of a syringe.

In additional exemplary aspects, the outer wall 60 of the elongate body 12 can define a recess 64 at the second end portion 92 of the elongate body. In these aspects, the recess 64 at the second end portion 92 can be configured to promote access to a syringe secured in the neutral position within the syringe holder 10.

In another aspect, the elongate body 12 can define a plurality of through-holes 15 extending between the top surface 16 and the bottom surface 18 of the elongate body. In this aspect, the plurality of through-holes 15 can be substantially aligned with the longitudinal axis 14 of the elongate body 12. In exemplary aspects, the plurality of through-holes 15 can be positioned such that at least one through-hole is positioned between at least one of: (a) the first and second rows 50a, 50b of projections 52, the second and third rows 50b, 50c of projections, the third and fourth rows 50c, 50d of projections, the first row 50a of projections and the first end portion 90 of the elongate body 12, and the fourth row 50d of projections and the second end portion 92 of the elongate body. It is contemplated that the plurality of through-holes 15 can be configured to promote improved penetration of steam and improved drainage of sterilization condensate during autoclave sterilization. In exemplary aspects, the plurality of through-holes can have a diameter ranging from about 0.05 inches to about 0.5 inches and, more preferably, ranging from about 0.1 inches to about 0.2 inches. In further exemplary aspects, it is contemplated that each through-hole 15 of the plurality of through-holes can be spaced from adjacent through-holes by a selected distance 19 ranging from about 0.5 inches to about 2 inches, and more preferably, ranging from about 1 inch to about 1.5 inches. In still further exemplary aspects, it is contemplated that each through-hole 15 of the plurality of through-holes can have a depth 17 (corresponding to the distance between the top surface 16 and the bottom surface 18) ranging from about 0.1 inches to about 0.2 inches.

In exemplary aspects, it is contemplated that the portions of the inner surfaces of the outer wall 60 most proximate the upper surface 16 of the elongate body 12 can curve outwardly with a radius of curvature ranging from about 0.1 inches to about 0.2 inches. In additional exemplary aspects, it is contemplated that the portions of the outer surfaces of the guard elements 20, supporting elements 40, and projections 52 most proximate the upper surface 16 of the elongate body 12 can curve outwardly with a radius of curvature ranging from about 0.1 inches to about 0.4 inches and, more preferably, ranging from about 0.1 inches to about 0.3 inches.

The Surgical Tray

As depicted in FIGS. 12-21, a surgical tray 100 can be provided for temporarily storing one or more surgical instruments in a neutral position during a surgical procedure. The surgical tray 100 can have a longitudinal axis 102. In exemplary aspects, the surgical tray 100 can have a longitudinal length 104 ranging front about 5 inches to about 15 inches and more preferably, ranging from about 10 inches to about 12 inches. In these aspects, the surgical tray 100 can have a width 106 ranging from about 2 inches to about 6 inches and, more preferably, ranging from about 3 inches to about 5 inches. In further exemplary aspects, the surgical tray 100 can have a height 108 ranging from about 1 inch to about 2 inches, and more preferably, ranging from about 1.1 inches to about 1.5 inches.

In one aspect, the surgical tray 100 can comprise a base portion 110 having a top surface 112 and a bottom surface 114. In this aspect, the base portion 110 can define an outer periphery 116 of the surgical tray 100. In exemplary aspects, the base portion 110 can have a thickness 115 measured from the top surface 112 to the bottom surface 114.

In another aspect, the surgical tray 100 can comprise an outer wall 120 extending upwardly relative to the top surface 112 of the base portion 110. In this aspect, outer wall 120 can have opposed proximal and distal end portions 122, 124 and first and second opposed side portions 126, 128. It is contemplated that at least the side portions 126, 128 of the outer wall 120 can be spaced relative to the outer periphery 116 of the surgical tray by a predetermined distance 127. In exemplary aspects, the outer wall 120 can have a thickness 125. In these aspects, it is optionally contemplated that the thickness 125 of the outer wall can be consistent. Alternatively, it is contemplated that the thickness 125 of the outer wall can be variable.

In an additional aspect, the surgical tray 100 can comprise an inner portion 130 positioned within the outer wall 120. In this aspect, the inner portion 130 can have a top surface 132, a plurality of projections 134, and a plurality of through-holes 136. It is contemplated that the plurality of projections 134 and the plurality of through-holes 136 can be spaced relative to the longitudinal axis 102 of the surgical tray 100. It is still further contemplated that each through-hole 136 of the plurality of through-holes can extend from the top surface 132 of the inner portion 130 to the bottom surface 114 of the base portion 110. Thus, it is contemplated that the inner portion 130 can have a thickness 131 (measured from the top surface 132 of the inner portion to the bottom surface 114 of the base portion 110) that is greater than the thickness 115 of the base portion. It is further contemplated that the outer wall 120 can cooperate with the inner portion 130 to define a cavity 138 configured to receive the one or more surgical instruments in the neutral position.

Figure 20A:
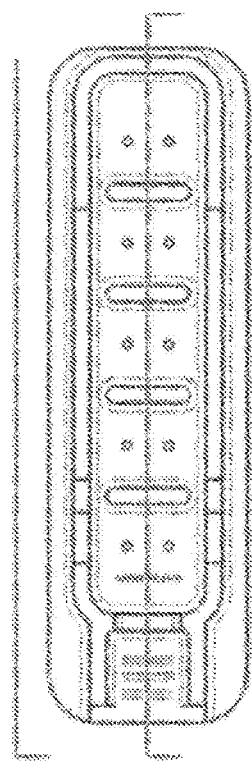
FIG. 20A is a top perspective view of an exemplary surgical tray.
Figure 20B:
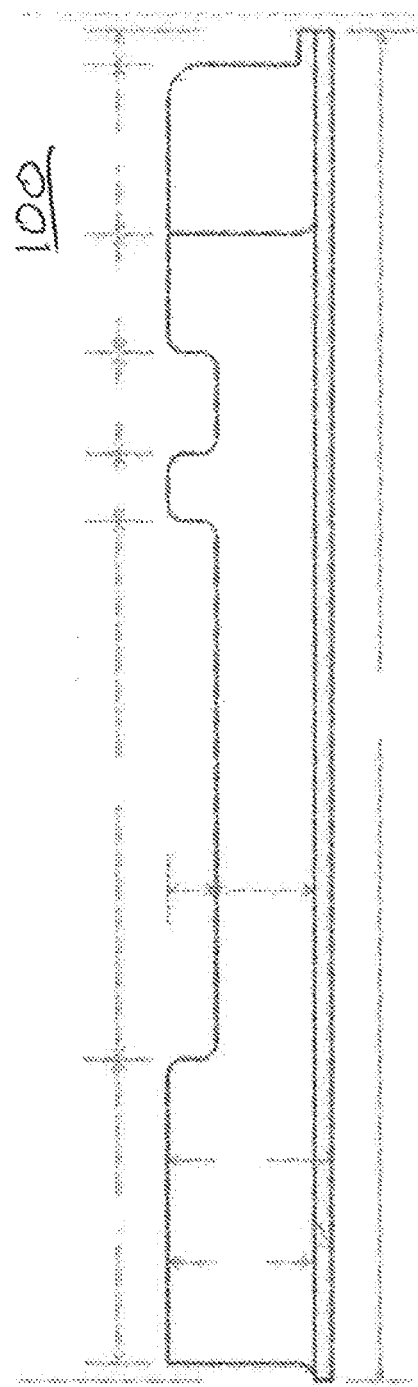
FIG. 20B is a side perspective view of the surgical tray of FIG. 20A, taken along line 20B.
Figure 20C:
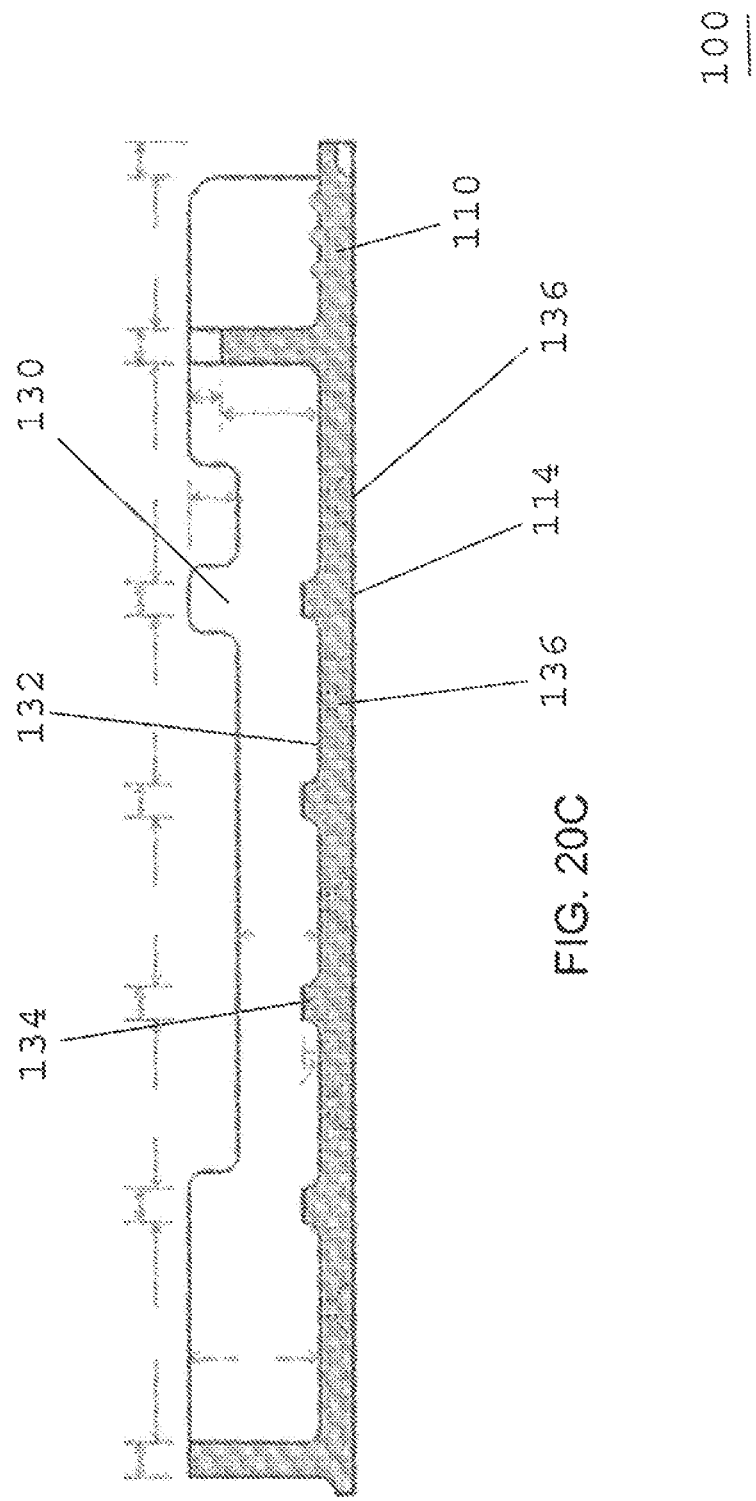
FIG. 20C is a longitudinal cross-sectional view of the surgical tray of FIG. 20A, taken along line 20C.
Figure 21:
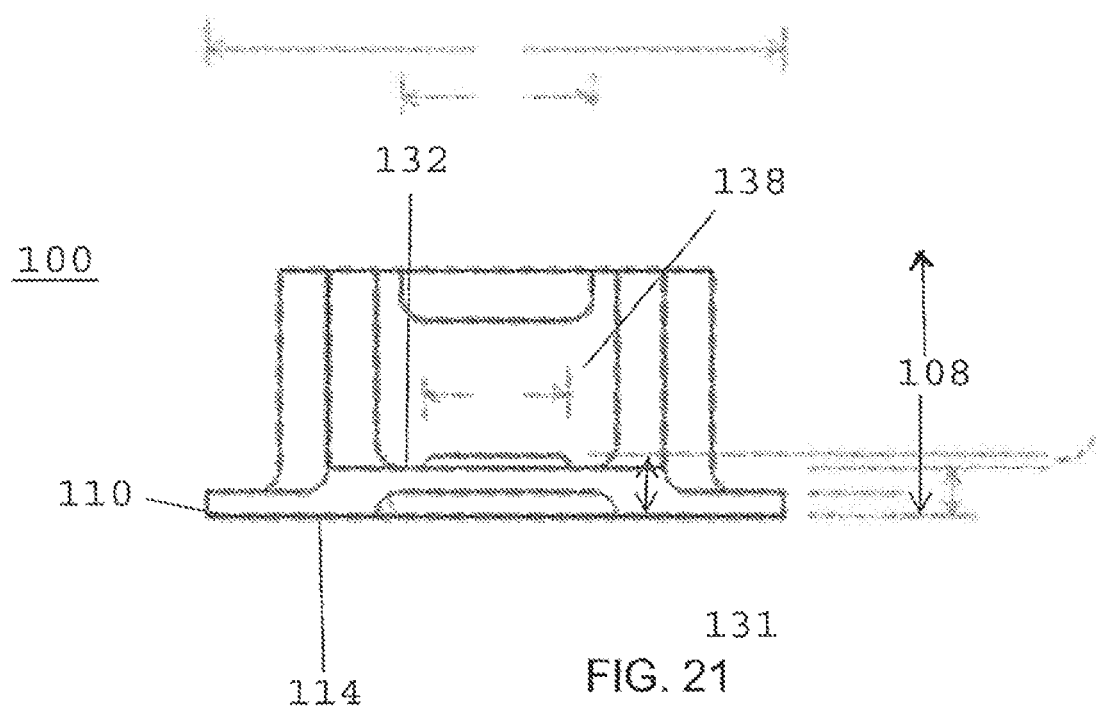
FIG. 21 is a front end view of an exemplary surgical tray as described herein, showing exemplary dimensions of the surgical tray.

In exemplary aspects, the plurality of through-holes 136 can comprise a plurality of rows 135 of at least one through-hole 136. Optionally, in some aspects, the plurality of projections 134 can comprise four projections. In these aspects, it is contemplated that the plurality of rows 135 of at least one through-hole 136 can comprise five rows of at least one through-hole, with a first row 135a of at least one through-hole being positioned between the proximal end portion 122 of the outer wall 120 and a first projection 134a of the plurality of projections, a second row 135b of at least one through-hole being positioned between the first projection 134a and a second projection 134b of the plurality of projections, a third row 135c of at least one through-hole being positioned between the second projection 134b and a third projection 134c of the plurality of projections, a fourth row 135d of at least one through-hole being positioned between the third projection 134c and a fourth projection 134d of the plurality of projections, and a fifth row 135e of at least one through-hole being positioned between the fourth projection 134d and the distal end portion 124 of the outer wall. It is contemplated that the through-holes 136 can be configured to promote improved penetration of steam and improved drainage of sterilization condensate during autoclave sterilization. In exemplary aspects, the plurality of through-holes 136 can have a diameter ranging from about 0.05 inches to about 0.5 inches and, more preferably, ranging from about 0.1 inches to about 0.2 inches. In still further exemplary aspects, and as shown in FIG. 20C, it is contemplated that each through-hole 136 can have a variable diameter. For example, in some aspects, it is contemplated that the diameter of the through-hole 136 can be greater proximate the bottom surface 114 of the base portion 110 than it is proximate the top surface 132 of the inner portion 130.

In additional exemplary aspects, each projection 134 cart have a longitudinal length 170 (measured relative to the longitudinal axis 102 of the surgical tray 100) ranging from about 0.1 inches to about 0.5 inches and more preferably, being about 0.25 inches. In these aspects, it is contemplated that each projection 134 can have a width 172 (measured perpendicularly relative to the longitudinal axis 102 of the surgical tray 100) ranging from about 0.75 inches to about 1.75 inches and more preferably, from about 1 inch to about 1.5 inches.

In exemplary aspects, the at least one through-hole 136 of each row 135 can comprise a pair of through-holes that are spaced from one another by a selected distance 137 ranging from about 0.25 inches to 1 inch and more preferably, ranging from about 0.5 inches to about 0.75 inches. In these aspects, it is contemplated that each pair of through-holes can be substantially evenly spaced relative to the respective first and second side portions 126, 128.

In further exemplary aspects, each row 135 of at least one through-hole 136 can be spaced from adjacent projections 134 by a selected distance 139 ranging from about 0.5 inches to about 1 inch and more preferably, ranging from about 0.7 to about 0.8 inches.

In additional aspects, the first and second side portions 126, 128 of the outer wall 120 can define respective first and second recesses 140, 142. In these aspects, the first recess 140 of the first side portion 126 can be substantially aligned with the first recess 140 of the second side portion 128 and the second recess 142 of the first side portion 126 can be substantially aligned with the second recess 142 of the second side portion 128. It is contemplated that the first and second recesses 140, 142 of the first and second side portions 126, 128 of the outer wall 120 can have respective lengths 144, 146 relative to the longitudinal axis 102 of the surgical tray 100. It is further contemplated that the lengths 144 of the first recesses 140 can be smaller than the lengths 146 of the second recesses 142. For example, it is contemplated that the lengths 144 of the first recesses 140 can range from about 0.5 inches to about 1.0 inches and, more preferably, can range from about 0.6 inches to about 0.9 inches. It is further contemplated that the lengths 146 of the second recesses 142 can range from about 3 inches to about 5 inches and, more preferably, can range from about 3.5 inches to about 4.5 inches. In exemplary aspects, it is contemplated that the proximal end portion 122 of the outer wall 120 can define a recess 148. In operation, it is contemplated that the first recesses 140, the second recesses 142, and the recess 148 can provide selected locations for more easily accessing surgical instruments positioned within the inner portion 130 of the surgical tray 100. In exemplary aspects, it is contemplated that the second recesses 142 can be configured to permit access to a shaft portion of a surgical instrument, while the first recesses 140 can be configured to permit access to an end portion of a surgical instrument. In exemplary aspects, the first recesses 140 of the first and second side portions 126, 128 can have a longitudinal length 141 (measured relative to the longitudinal axis 102 of the surgical tray 100) ranging from about 0.5 inches to about 1 inch and more preferably, being about 0.75 inches. In other exemplary aspects, the second recesses 142 of the first and second side portions 126, 128 can have a longitudinal length 143 (measured relative to the longitudinal axis 102 of the surgical tray 100) ranging from about 3 inches to about 5 inches and more preferably, being about 4 inches. In further exemplary aspects, it is contemplated that the first and second recesses 140, 142 can have a depth 145 ranging from about 0.2 inches to about 0.5 inches.

Figure 12:
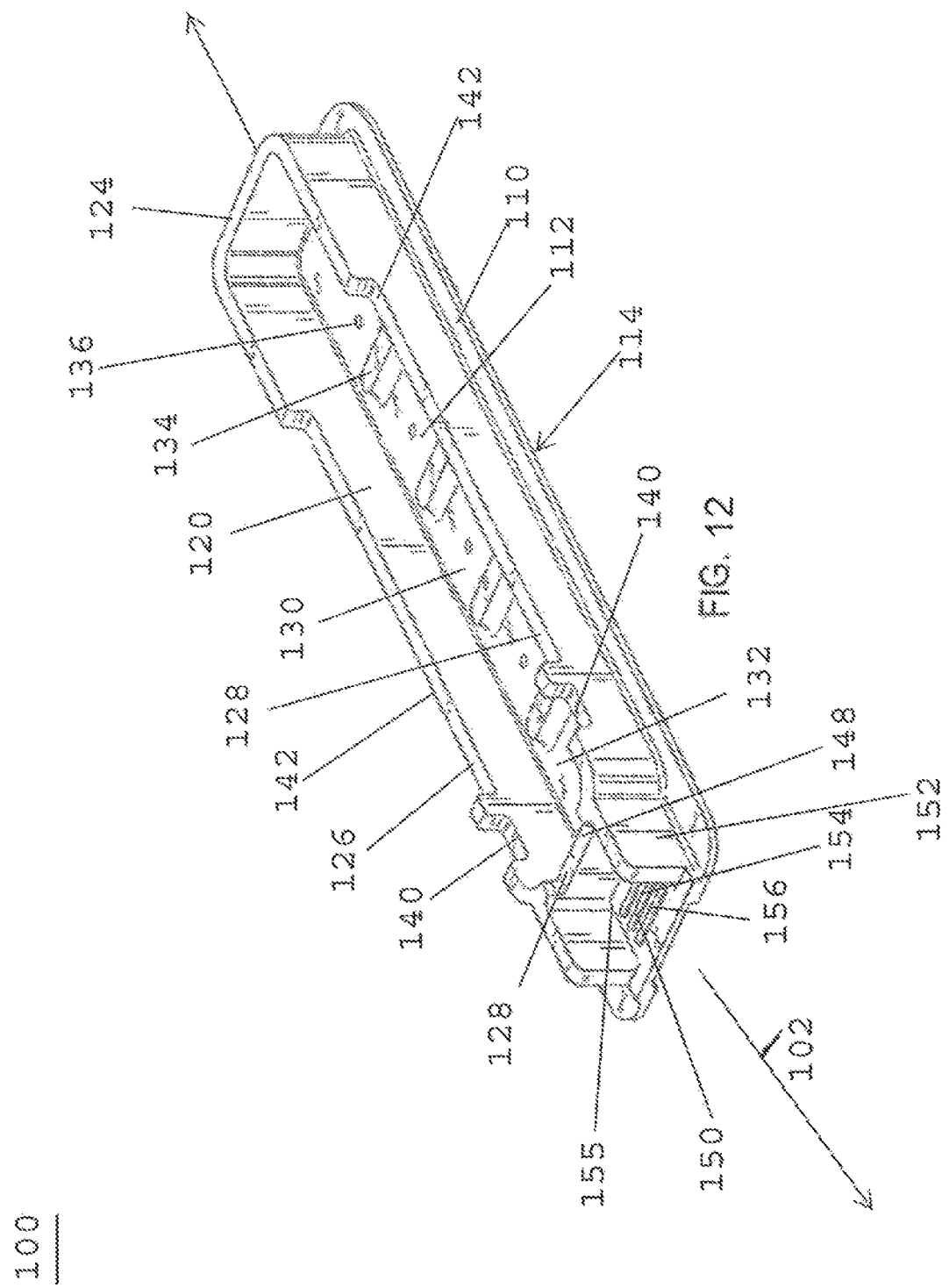
FIG. 12 is a perspective view of an exemplary surgical tray for receiving one or more surgical instruments, as described herein.
Figure 13:
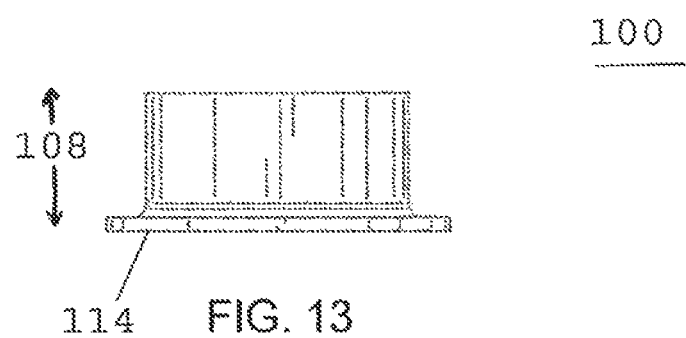
FIG. 13 is a back end view of the surgical tray of FIG. 12.
Figure 14:
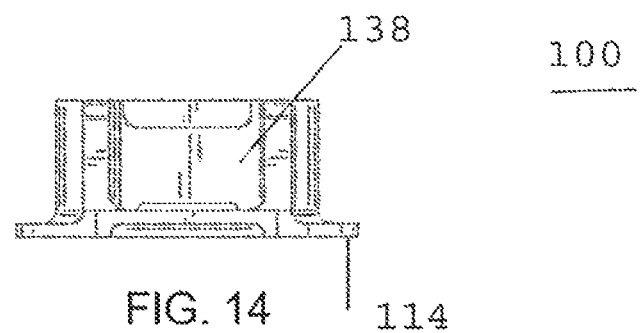
FIG. 14 is a front end view of the surgical tray of FIG. 12.
Figure 15:
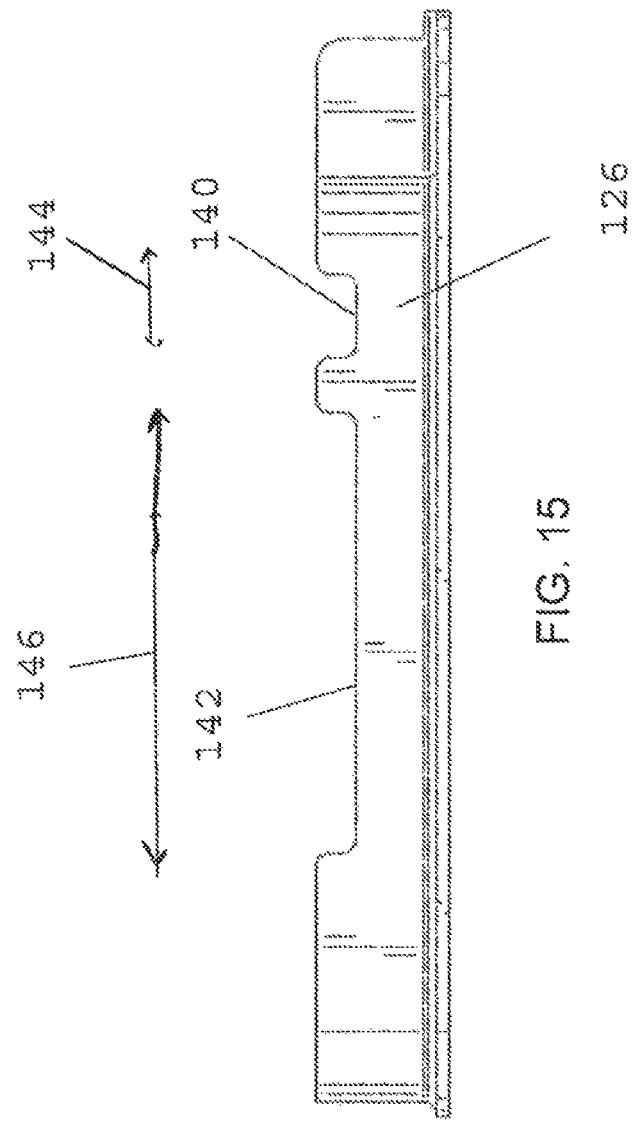
FIG. 15 is a left side view of the surgical tray of FIG. 12.
Figure 16:
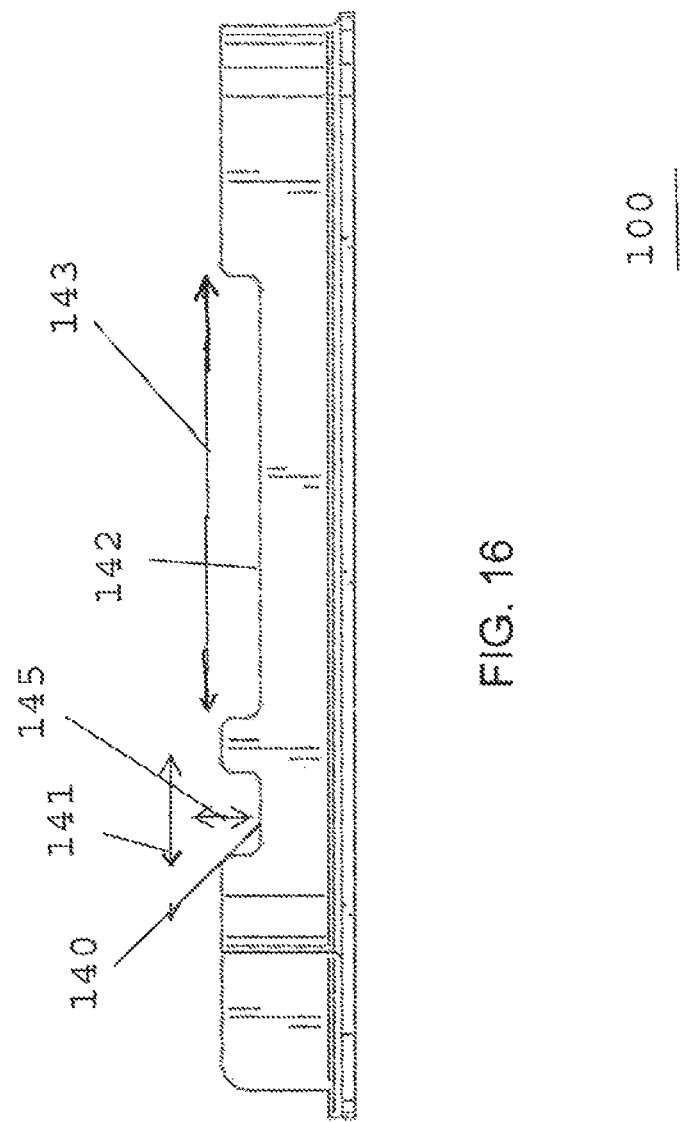
FIG. 16 is a right side view of the surgical tray of FIG. 12.
Figure 17:
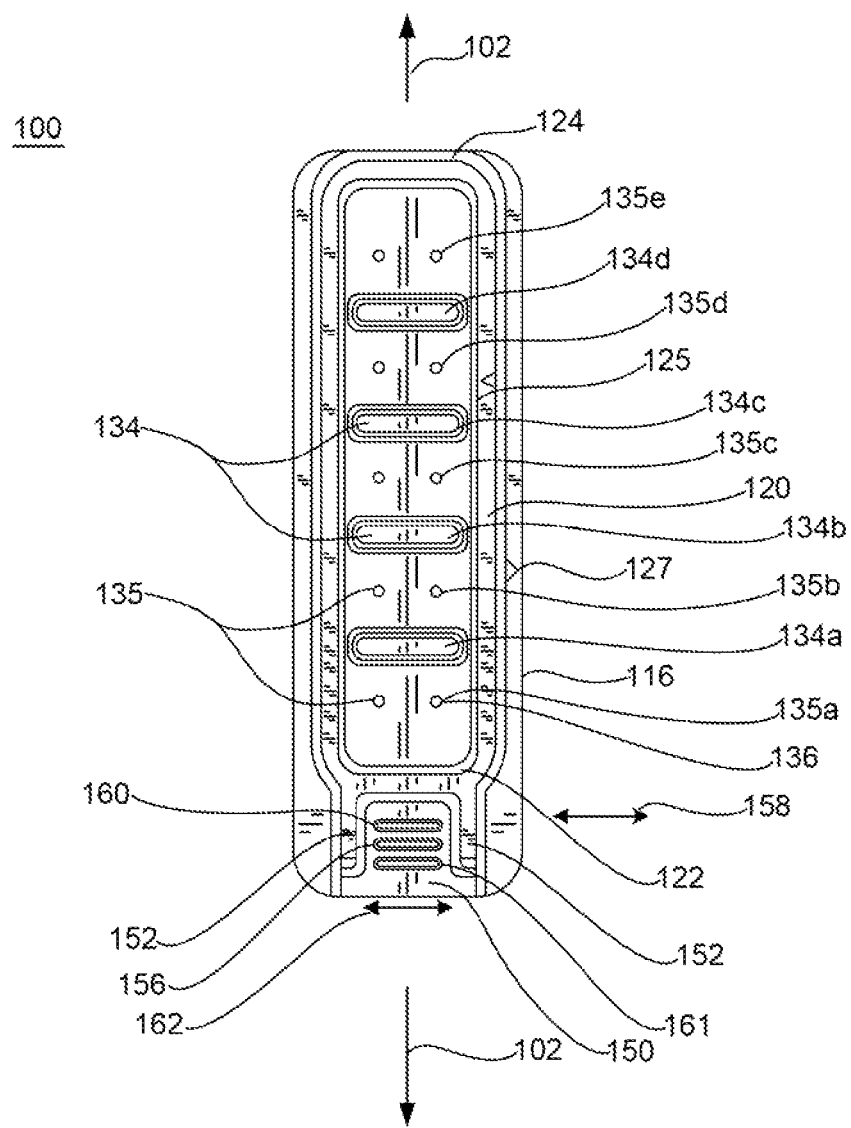
FIG. 17 is a top view of the surgical tray of FIG. 12.
Figure 18:
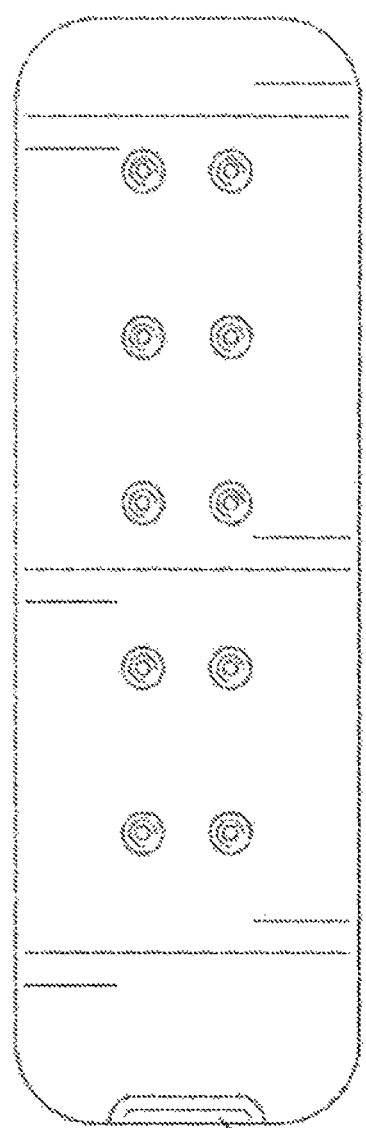
FIG. 18 is a bottom view of the surgical tray of FIG. 12.
Figure 19:
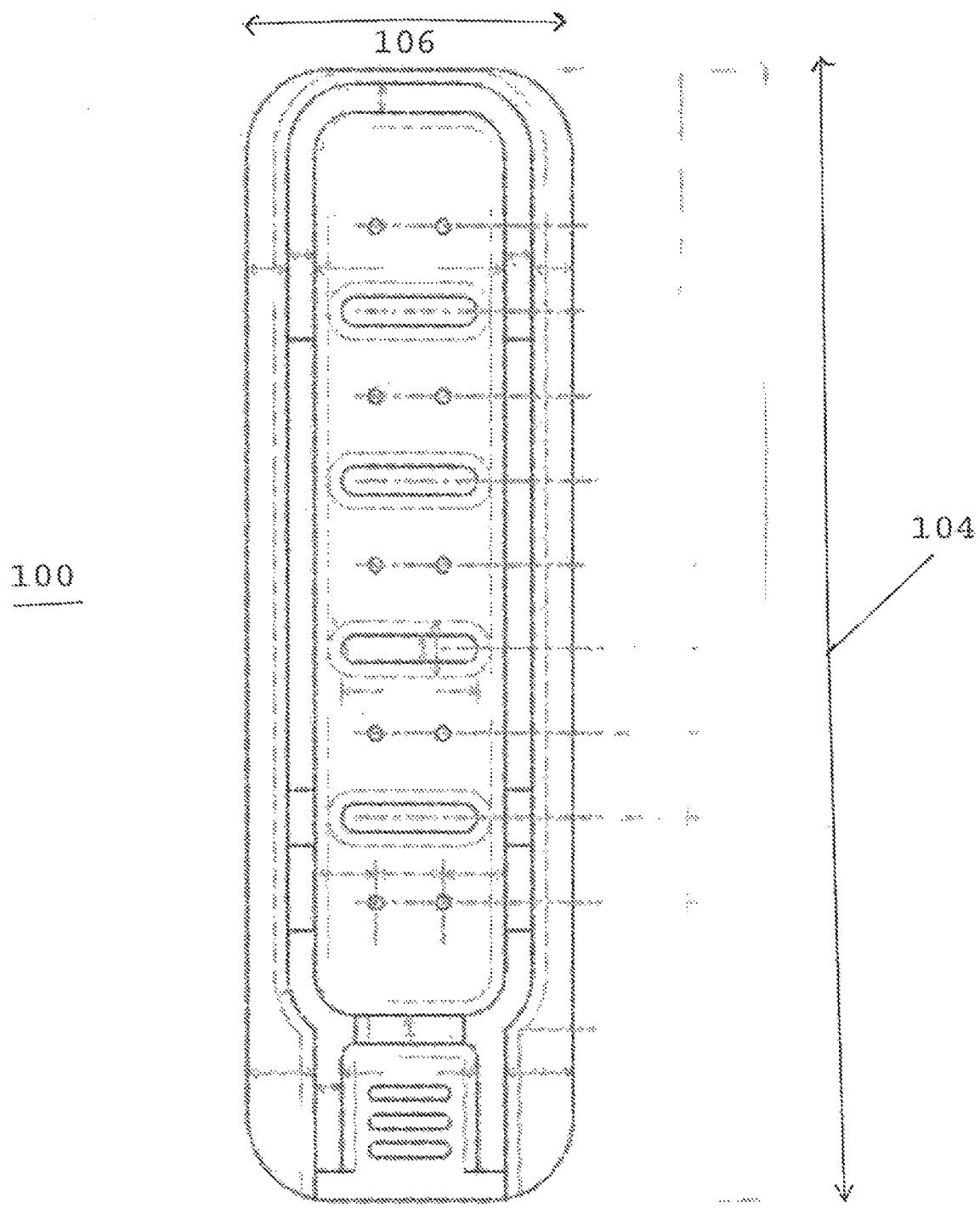
FIG. 19 is a top view of an exemplary surgical tray as described herein, showing exemplary dimensions of the surgical tray.

In a further aspect, the surgical tray 100 can further comprise an engagement portion 150 positioned proximate the proximal end portion 122 of the outer wall 120. In this aspect, the engagement portion 150 can comprise first and second spaced support elements 152 connected to the proximal end portion 122 of the outer wall 120. As shown in FIGS. 12 and 17, the first and second spaced support elements 152 can extend outwardly from the proximal end portion 122 of the outer wall substantially parallel to the longitudinal axis 102 of the surgical tray 100. In another aspect, the engagement portion 150 can further comprise an engagement surface 154 positioned between the proximal end portion 122 of the outer wall and the first and second support elements 152. In this aspect, the engagement surface 154 can be configured for contact with one or more fingers of a user. In a further aspect, the proximal end portion 122, the first and second support elements 152, and the engagement surface 154 can cooperate to define a receiving space 155 configured for receipt of one or more fingers of a user. In an additional aspect, the engagement portion 150 can further comprise a plurality of projections 156 extending upwardly relative to the engagement surface 154. In this aspect, the plurality of projections 156 can be spaced relative to the longitudinal axis 102 of the surgical tray 100. It is contemplated that each projection 156 of the plurality of projections can have a longitudinal axis 158 oriented substantially perpendicularly relative to the longitudinal axis 102 of the surgical tray 100. It is further contemplated that each projection 156 cart have a longitudinal length 160 (measured relative to longitudinal axis 158) ranging from about 0.25 inches to about 1.25 inches and, more preferably, ranging from about 0.5 inches to about 1 inch. It is still further contemplated that each projection can have a height 161 ranging from about 0.05 inches to about 0.15 inches. In exemplary aspects, the receiving space 155 can have a width 162 (measured perpendicularly relative to the longitudinal axis 102 of the surgical tray 100) ranging from about 0.5 inches to about 2.5 inches and, more preferably, ranging from about 1 inch to about 1.5 inches.

In exemplary aspects, the base portion 110 can cooperate with the engagement portion 150 to define a notch 118 extending underneath at least a portion of the engagement surface 154 of the engagement portion 150. In these aspects, the notch 118 can be configured to receive one or more fingers of a user. In exemplary aspects, contemplated that one or more fingers of a user can be received in the receiving space 155 while one or more other fingers of the user are received within the notch 118. Upon gripping of the engagement portion 150 and/or the notch 118 by a user, it is contemplated that the user can shift and/or lift the surgical tray 100 to a desired position.

In exemplary aspects, it is contemplated that the portions of the inner surfaces of the outer wall 120 most proximate the top surface 132 of the inner portion 130 can curve outwardly with a radius of curvature ranging from about 0.1 inches to about 0.8 inches. In additional exemplary aspects, it is contemplated that the portions of the outer surfaces of the projections 134 most proximate the top surface 132 of the inner portion 130 can curve outwardly with a radius of curvature ranging from about 0.1 inches to about 0.4 inches and, more preferably, ranging from about 0.1 inches to about 0.3 inches.

Exemplary Aspects

In exemplary aspects, disclosed herein is an autoclave-tolerant container configured to receive one or more surgical instruments in a neutral position during a surgical procedure, wherein the container is configured to withstand autoclave sterilization such that the container is reusable following autoclave sterilization.

In additional exemplary aspects, the autoclave-tolerant container comprises a syringe holder for securing at least one syringe in a neutral position during a surgical procedure, each syringe having a needle, a barrel, and a plunger, the syringe holder comprising: an elongate body having a longitudinal axis, a top surface, and a bottom surface; at least one pair of spaced guard elements extending upwardly relative to the top surface of the elongate body, each guard element of each pair of guard elements having first and second end portions and a longitudinal axis extending substantially parallel to the longitudinal axis of the elongate body, each pair of spaced guard elements cooperating to define a channel configured to receive at least a portion of the needle of a syringe; at least one supporting element extending upwardly relative to the top surface of the elongate body, each supporting element having a longitudinal axis extending substantially perpendicularly relative to the longitudinal axis of the elongate body, each supporting element being spaced from the first end portions of a pair of guard elements relative to the longitudinal axis of the elongate body such that the pair of guard elements and the supporting element cooperate to define a receiving space configured to receive at least a portion of the needle of a syringe; and at least one row of spaced projections extending upwardly relative to the top surface of the elongate body, the spaced projections of each row cooperating to define at least one channel configured to receive a portion of the barrel of the syringe, the plurality of projections extending substantially perpendicularly relative to the longitudinal axis of the elongate body, wherein each channel defined by each row of spaced projections is substantially axially aligned with the channel defined by a pair of spaced guard elements.

In other exemplary aspects, the elongate body comprises an outer wall, the outer wall extending upwardly relative to the top surface of the elongate body.

In other exemplary aspects, the guard elements of the at least one pair of spaced guard elements and the supporting element have respective heights relative to the top surface of the elongate body, and the heights of each pair of spaced guard elements are substantially equal.

In other exemplary aspects, the height of each supporting element of the at least one supporting element is substantially equal to the heights of the at least one pair of spaced guard elements.

In other exemplary aspects, the outer wall of the elongate body has a height relative to the top surface of the elongate body, and the height of the outer wall is less than the heights of the at least one pair of spaced guard elements and the at least one supporting element.

In other exemplary aspects, each projection of the at least one row of spaced projections has a respective height, the heights of the projections of the at least one row of spaced projections are substantially equal, and the heights of the projections are less than the height of the outer wall.

In other exemplary aspects, each supporting element of the at least one supporting element comprises: an engagement portion extending substantially parallel to the longitudinal axis of the supporting element, the engagement portion defining an engagement surface and an opposed back surface, the engagement surface being spaced a predetermined distance from the first end portions of the at least one row of spaced guard elements relative to the longitudinal axis of the elongate body; and a stabilizing portion extending from the back surface of the engagement portion substantially perpendicularly relative to the longitudinal axis of the supporting element.

In other exemplary aspects, the at least one pair of spaced guard elements comprises two pairs of spaced guard elements, the at least one supporting element comprises two supporting elements, and the two pairs of spaced guard elements and the two supporting elements are evenly positioned on opposing sides of the longitudinal axis of the elongate body.

In other exemplary aspects, each row of the at least one row of spaced projections comprises three projections, the three projections comprising two outer projections and a central projection, the two outer projections being evenly positioned on opposing sides of the longitudinal axis of the elongate body, the central projection being bisected by the longitudinal axis of the elongate body.

In other exemplary aspects, the at least one row of spaced projections comprises four rows of spaced projections, and a first row of spaced projections is spaced a predetermined distance from the second end portions of the pairs of spaced guard elements.

In other exemplary aspects, a second row of spaced projections is spaced a predetermined distance from the first row of spaced projections relative to the longitudinal axis of the elongate body, a third row of spaced projections is spaced a predetermined distance from the second row of spaced projections relative to the longitudinal axis of the elongate body, and a fourth row of spaced projections is spaced a predetermined distance from the third row of spaced projections relative to the longitudinal axis of the elongate body.

In other exemplary aspects, the predetermined distance by which the second row of spaced projections is spaced from the first row of spaced projections is substantially equal to the predetermined distance by which the third row of spaced projections is spaced from the second row of spaced projections and the predetermined distance by which the fourth row of spaced projections is spaced from the third row of spaced projections.

In other exemplary aspects, the elongate body has a first end portion and a second end portion, the first end portion is spaced from the at least one supporting element by a predetermined distance relative to the longitudinal axis of the elongate body, the second end portion is spaced from the fourth row of spaced projections by a predetermined distance relative to the longitudinal axis, and the space between the fourth row of spaced projections and the second end portion of the elongate body is configured to receive at least a portion of the plunger of a syringe.

In other exemplary aspects, the outer wall of the elongate body defines a recess at the second end portion of the elongate body, and the recess at the second end portion is configured to promote access to a syringe secured in the neutral position.

In other exemplary aspects, the elongate body defines a plurality of through-holes extending between the top surface and the bottom surface of the elongate body, and the plurality of holes are substantially aligned with the longitudinal axis of the elongate body.

In other exemplary aspects, the syringe holder comprises silicone.

In additional exemplary aspects, the autoclave-tolerant container comprises a surgical tray for temporary storage of one or more surgical instruments in a neutral position during a surgical procedure, the surgical tray having a longitudinal axis and comprising: a base portion having a top surface and a bottom surface, the base portion defining an outer periphery of the surgical tray; an outer wall extending upwardly relative to the top surface of the base portion, the outer wall having opposed proximal and distal end portions and first and second opposed side portions, wherein at least the side portions of the outer wall are spaced relative to the outer periphery of the surgical tray, the outer wall defining a cavity configured to receive the one or more surgical instruments; an inner portion positioned within the outer wall, the inner portion having a top surface, a plurality of projections, and a plurality of through-holes, the plurality of projections and the plurality of through-holes being spaced relative to the longitudinal axis of the surgical tray, each through-hole of the plurality of through extending from the top surface of the inner portion to the bottom surface of the base portion.

In other exemplary aspects, the plurality of through-holes comprise a plurality of rows of at least one through-hole.

In other exemplary aspects, the plurality of projections comprises four projections.

In other exemplary aspects, the plurality of rows of at least one through-hole comprise five rows of at least one through-hole, a first row of at least one through-hole is positioned between the proximal end portion of the outer wall and a first projection of the plurality of projections, a second row of at least one through-hole is positioned between the first projection and a second projection of the plurality of projections, a third row of at least one through-hole is positioned between the second projection and a third projection of the plurality of projections, a fourth row of at least one through-hole is positioned between the third projection and a fourth projection of the plurality of projections, and a fifth row of at least one through-hole is positioned between the fourth projection and the distal end portion of the outer wall.

In other exemplary aspects, the first and second side portions of the outer wall define respective first and second recesses, the first recess of the first side portion is substantially aligned with the first recess of the second side portion, and the second recess of the first side portion is substantially aligned with the second recess of the second side portion.

In other exemplary aspects, the first and second recesses of the first and second side portions of the outer wall have respective lengths relative to the longitudinal axis of the surgical tray, and the lengths of the first recesses are smaller than the lengths of the second recesses.

In other exemplary aspects, the proximal end portion of the outer wall defines a recess.

In other exemplary aspects, the surgical tray further comprises an engagement portion positioned proximate the proximal end portion of the outer wall, the engagement portion comprising: first and second spaced support elements connected to the proximal end portion of the outer wall, the first and second spaced support elements extending outwardly from the proximal end portion of the outer wall substantially parallel to the longitudinal axis of the surgical tray.

In other exemplary aspects, the engagement portion further comprises an engagement surface positioned between the proximal end portion of the outer wall and the first and second support elements, and the engagement portion is configured for contact with one or more fingers of a user.

In other exemplary aspects, the engagement portion further comprises a plurality of projections extending upwardly relative to the engagement surface.

In other exemplary aspects, the plurality of projections are spaced relative to the longitudinal axis of the surgical tray.

In other exemplary aspects, the base portion defines a notch positioned underneath the engagement surface of the engagement portion, the notch of the base portion being configured to receive one or more fingers of a user.

In other exemplary aspects, the surgical tray comprises silicone.

In further exemplary aspects, a method of using an autoclave-tolerant container is disclosed, comprising: positioning one or more surgical instruments in the autoclave-tolerant container during a first surgical procedure; removing the one or more surgical instruments from the autoclave-tolerant container; subjecting the autoclave-tolerant container to a autoclave sterilization procedure; and positioning one or more surgical instruments in the autoclave-tolerant container during a second surgical procedure.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A surgical tray for temporary storage of one or more surgical instruments in a neutral position during a surgical procedure, the surgical tray having a longitudinal axis and comprising:
   a base portion having a bottom surface, the base portion defining an outer periphery of the surgical tray;
   an outer wall extending from the base portion, the outer wall having opposed proximal and distal end portions and first and second opposed side portions, wherein the outer wall defines a cavity configured to receive the one or more surgical instruments; and
   an inner portion positioned within the outer wall, the inner portion having a top surface, a plurality of projections, and a plurality of through-holes, the plurality of projections and the plurality of through-holes being spaced relative to the longitudinal axis of the surgical tray, each through-hole of the plurality of through-holes extending from the top surface of the inner portion to the bottom surface of the base portion, wherein the surgical tray is configured to withstand autoclave sterilization, wherein the plurality of through-holes comprises a plurality of rows of through-holes, and wherein the plurality of rows of through-holes comprise five rows of at least one through-hole, wherein a first row of at least one through-hole is positioned between the proximal end portion of the outer wall and a first projection of the plurality of projections, wherein a second row of at least one through-hole is positioned between the first projection and a second projection of the plurality of projections, wherein a third row of at least one through-hole is positioned between the second projection and a third projection of the plurality of projections, wherein a fourth row of at least one through-hole is positioned between the third projection and a fourth projection of the plurality of projections, and wherein a fifth row of at least one through-hole is positioned between the fourth projection and the distal end portion of the outer wall.

2. The surgical tray of claim 1, further comprising an engagement portion positioned proximate the proximal end portion of the outer wall, the engagement portion comprising: first and second spaced support elements connected to the proximal end portion of the outer wall, the first and second spaced support elements extending outwardly from the proximal end portion of the outer wall substantially parallel to the longitudinal axis of the surgical tray.

3. The surgical tray of claim 2, wherein the engagement portion further comprises an engagement surface positioned between the proximal end portion of the outer wall and the first and second support elements, wherein the engagement portion is configured for contact with one or more fingers of a user.

4. The surgical tray of claim 3, wherein the base portion defines a notch positioned underneath the engagement surface of the engagement portion, the notch of the base portion being configured to receive one or more fingers of a user.

5. The surgical tray of claim 1, wherein the surgical tray comprises silicone.

6. The surgical tray of claim 1, wherein the surgical tray is made of a material consisting of silicone.

7. The surgical tray of claim 1, wherein each of the plurality of through-holes is configured to promote a penetration of steam and a drainage of a sterilization condensate during autoclave sterilization.

8. The surgical tray of claim 1, wherein each of the plurality of through-holes is spaced from a projection by 0.5 to 1.0 inch.

9. An autoclave-tolerant container configured to receive one or more surgical instruments in a neutral position during a surgical procedure, the autoclave-tolerant container comprising:
   an elongate body having a longitudinal axis, a top surface, and a bottom surface;
   an outer wall, the outer wall extending upwardly relative to the top surface of the elongate body; and
   at least one row of a plurality of spaced projections extending upwardly relative to the top surface of the elongate body, the spaced projections extending substantially perpendicularly relative to the longitudinal axis of the elongate body, wherein the elongate body defines a plurality of through-holes extending between the top surface and the bottom surface of the elongate body, wherein the autoclave-tolerant container is configured to withstand autoclave sterilization such that the autoclave-tolerant container is reusable following autoclave sterilization, wherein the plurality of spaced projections comprises four projections, wherein the plurality of through-holes comprise five rows of at least one through-hole, wherein a first row of at least one through-hole is positioned between a proximal end portion of the outer wall and a first projection of the plurality of spaced projections, wherein a second row of at least one through-hole is positioned between the first projection and a second projection of the plurality of spaced projections, wherein a third row of at least one through-hole is positioned between the second projection and a third projection of the plurality of spaced projections, wherein a fourth row of at least one through-hole is positioned between the third projection and a fourth projection of the plurality of spaced projections, and wherein a fifth row of at least one through-hole is positioned between the fourth projection and a distal end portion of the outer wall.

\* \* \* \* \*